United States Patent
Single et al.

(10) Patent No.: US 12,102,827 B2
(45) Date of Patent: Oct. 1, 2024

(54) SUPERVISOR FOR IMPLANTABLE STIMULATION DEVICES

(71) Applicant: Saluda Medical Pty Limited, Artarmon (AU)

(72) Inventors: Peter Single, Artarmon (AU); Dean Karantonis, Maroubra (AU); Robert Gorman, Randwick (AU); Milan Obradovic, Beacon Hill (AU); Ivan Guelton, Artarmon (AU); Michael Narayanan, Artarmon (AU)

(73) Assignee: Saluda Medical Pty Limited, Macquarie Park (AU)

( * ) Notice: Subject to any disclaimer, the term of this patent is extended or adjusted under 35 U.S.C. 154(b) by 613 days.

(21) Appl. No.: 17/285,407

(22) PCT Filed: Oct. 23, 2019

(86) PCT No.: PCT/AU2019/051164
§ 371 (c)(1),
(2) Date: Apr. 14, 2021

(87) PCT Pub. No.: WO2020/082129
PCT Pub. Date: Apr. 30, 2020

(65) Prior Publication Data
US 2021/0379383 A1    Dec. 9, 2021

(30) Foreign Application Priority Data
Oct. 23, 2018  (AU) .................................. 2018904015

(51) Int. Cl.
*A61N 1/00* (2006.01)
*A61N 1/02* (2006.01)
(Continued)

(52) U.S. Cl.
CPC ......... *A61N 1/36139* (2013.01); *A61N 1/025* (2013.01); *A61N 1/0551* (2013.01);
(Continued)

(58) Field of Classification Search
None
See application file for complete search history.

(56) References Cited

U.S. PATENT DOCUMENTS 5,658,322 A * 8/1997 Fleming .................. A61N 1/40
                                                                607/66
2002/0010414 A1 * 1/2002 Coston .................. A61N 1/325
                                                                604/20
(Continued)

FOREIGN PATENT DOCUMENTS

WO    WO 2006/055849       5/2006
WO    WO-2006055849 A1 *   5/2006 ......... A61N 1/36053
(Continued)

OTHER PUBLICATIONS

International Preliminary Report for Patentability for International Application No. PCT/AU2019/050164, Issued Apr. 27, 2021, 7 pgs.
(Continued)

*Primary Examiner* — John R Downey
*Assistant Examiner* — Anant A Gupta
(74) *Attorney, Agent, or Firm* — Barnes & Thornburg LLP

(57) ABSTRACT

This disclosure relates to implantable neuro stimulation devices with a feedback loop to control an amount of energy delivered into a neural tissue based on a measured evoked neural response. Stimulation electrodes deliver stimulation energy to neural tissue. A microprocessor performs closed-loop control of the stimulation energy based on a feedback signal that is indicative of an evoked neural response. A supervisor is connected to the feedback signal and detects
(Continued)

malfunction of the stimulator based on the feedback signal. The supervisor is also connected to the stimulator to provide a status signal to the stimulator and changes the status signal to indicate malfunction upon detecting malfunction based on the feedback signal. The microprocessor adjusts the control of the stimulation energy in response to the status signal from the supervisor indicating malfunction.

33 Claims, 7 Drawing Sheets

(51) Int. Cl.
*A61N 1/05* (2006.01)
*A61N 1/16* (2006.01)
*A61N 1/36* (2006.01)
*H02J 50/10* (2016.01)

(52) U.S. Cl.
CPC ........... *A61N 1/16* (2013.01); *A61N 1/36125* (2013.01); *H02J 50/10* (2016.02)

(56) References Cited

U.S. PATENT DOCUMENTS

| | | | | |
|---|---|---|---|---|
| 2003/0045906 A1* | 3/2003 | Stroebel | ............... | A61N 1/3975 607/5 |
| 2003/0097157 A1* | 5/2003 | Wohlgemuth | ....... | A61N 1/3704 607/27 |
| 2012/0290040 A1 | 11/2012 | Moffitt et al. | | |
| 2013/0245718 A1 | 9/2013 | Birkholtz et al. | | |
| 2014/0236257 A1 | 8/2014 | Parker et al. | | |
| 2014/0277288 A1 | 9/2014 | Archer | | |
| 2015/0066006 A1 | 3/2015 | Srivastava | | |
| 2015/0151120 A1* | 6/2015 | Saar | ....................... | A61N 1/325 604/20 |
| 2016/0287126 A1 | 10/2016 | Parker et al. | | |
| 2017/0361101 A1 | 12/2017 | Single | | |
| 2021/0379379 A1* | 12/2021 | Campean | ........... | A61N 1/36031 |

FOREIGN PATENT DOCUMENTS

WO WO-2017184753 A1 * 10/2017 ........... A61N 1/3601
WO 2020082129 A1 4/2020

OTHER PUBLICATIONS

Australian Patent Office, International Search Report and Written Opinion of the International Searching Authority, International Application No. PCT/AU2019/050164, Dec. 9, 2019, 19 pages.

* cited by examiner

Energy and data are transmitted in different channels (data in RF communication channels and energy via inductive link)

SUPERVISOR FOR IMPLANTABLE STIMULATION DEVICES

RELATED APPLICATIONS

This application claims priority from Australian Provisional Application 2018904015 filed on 23 Oct. 2018, which is included herein by reference in its totality.

TECHNICAL FIELD

This disclosure relates to implantable neuro stimulation devices with a feedback loop to control an amount of energy delivered into a neural tissue based on a measured evoked neural response.

BACKGROUND

Implantable neuro-stimulation devices provide significant benefits to patients suffering from chronic pain and other diseases. These devices may include sophisticated control algorithms that adjust stimulation output in a closed-loop control paradigm, such as PID control, which can be implemented as software running on a microprocessor.

However, the use of software may bear the risk of software glitches, bugs, coding errors, soft errors and other unforeseen malfunctions. Such circumstances can lead to significant discomfort to the patient and in particular, over-stimulation that may be more painful that the actual pain that is being addressed by the stimulation at the first place.

In particular, when a control loop measures the evoked response, a change in posture by the patient, for example, may change the sensitivity, which, in turn, may change the loop gain and the loop may oscillate. In other words, the threshold and slope of response curve changes when patient moves, which makes closed-loop control difficult.

Any discussion of documents, acts, materials, devices, articles or the like which has been included in the present specification is not to be taken as an admission that any or all of these matters form part of the prior art base or were common general knowledge in the field relevant to the present disclosure as it existed before the priority date of each claim of this application.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

SUMMARY

An implantable neuro-stimulation device comprises:
one or more stimulation electrodes configured to deliver stimulation energy to neural tissue;
a stimulator comprising a microprocessor and program memory with program code stored thereon, the program code, when executed by the microprocessor, causing the microprocessor to perform closed-loop control of the stimulation energy based on a feedback signal that is indicative of an evoked neural response;
a supervisor
connected to the feedback signal,
configured to detect malfunction of the stimulator based on the feedback signal;
connected to the stimulator to provide a status signal to the stimulator; and
configured to change the status signal to indicate malfunction upon detecting malfunction based on the feedback signal;
wherein the microprocessor is configured to adjust the control of the stimulation energy in response to the status signal from the supervisor indicating malfunction.

The feedback signal may be indicative of a feedback value representing one or more of:
measured evoked response,
late response, and
evoked muscle response; and
the supervisor may be configured to compare the feedback value to a desired feedback value and to change the status signal based on the comparison to indicate malfunction.

The processor may be configured to reduce the desired feedback value upon the status signal indicating malfunction.

The processor may be configured to half the desired feedback value upon the status signal indicating malfunction.

The processor may be configured to perform mitigation upon the status signal indicating malfunction after reducing the desired feedback value.

The supervisor may be connected to the feedback signal through an amplifier that amplifies the feedback signal to detect clipping of the amplifier and the supervisor is configured to change the status signal to indicate malfunction based on the clipping of the amplifier.

The supervisor may be connected to a stimulation intensity signal that is indicative of a stimulation intensity and the supervisor may be configured to compare the instant stimulation intensity signal to a maximum value and change the status signal to indicate malfunction upon determining that the stimulation intensity was at the maximum value for a predetermined period of time.

The supervisor may be configured to change the status signal to indicate malfunction upon determining that the stimulation intensity is at a maximum value and a feedback value as indicated by the feedback signal is less than a desired feedback value.

The processor may be configured to reduce the desired feedback value upon detecting malfunction based on the status signal and to perform mitigation upon determining that the malfunction is present after reducing the desired feedback value.

The supervisor may be further connected to one or more clock signals and configured to detect a clock error based on the one or more clock signals and change the status signal to malfunction upon determining a clock error.

The stimulator may be further configured to adjust the control of the stimulation energy in response to an out of compliance signal indicating malfunction.

The status signal may be provided to the microprocessor as an interrupt signal.

The microprocessor may be configured to adjust the control of the stimulation energy by one or more of:
stopping stimulation;
adjusting an amplifier gain of a feed-back loop;
adjusting a stimulation level; or
enabling/disabling closed-loop therapy.

The microprocessor or the supervisor may be configured to detect a possible noise condition in the feedback signal and, upon detecting a possible noise condition in the feedback signal, to change the control of the stimulation energy.

Determining the possible noise condition may comprise detecting a charging event.

Detecting a possible noise condition may be based on a signal indicating that a charging event is anticipated.

Changing the control of the stimulation energy may comprise switching the control to open-loop control during the possible noise condition and switching back to closed-loop control upon determining absence of the possible noise condition.

A method for neuro-stimulation comprises:
executing program code to perform closed-loop control of stimulation energy based on a feedback signal that is indicative of an evoked neural response;
providing the stimulation energy to one or more stimulation electrodes for delivery into neural tissue;
monitoring the delivery of energy to the stimulation electrodes by monitoring the feedback signal; and
adjusting the control of the stimulation energy in response to the monitoring indicating malfunction of the stimulation.

Optional features described of any aspect of method, computer readable medium or computer system, where appropriate, similarly apply to the other aspects also described here.

BRIEF DESCRIPTION OF DRAWINGS

An example will now be described with reference to the following drawings.

DESCRIPTION OF EMBODIMENTS

Figure 1:
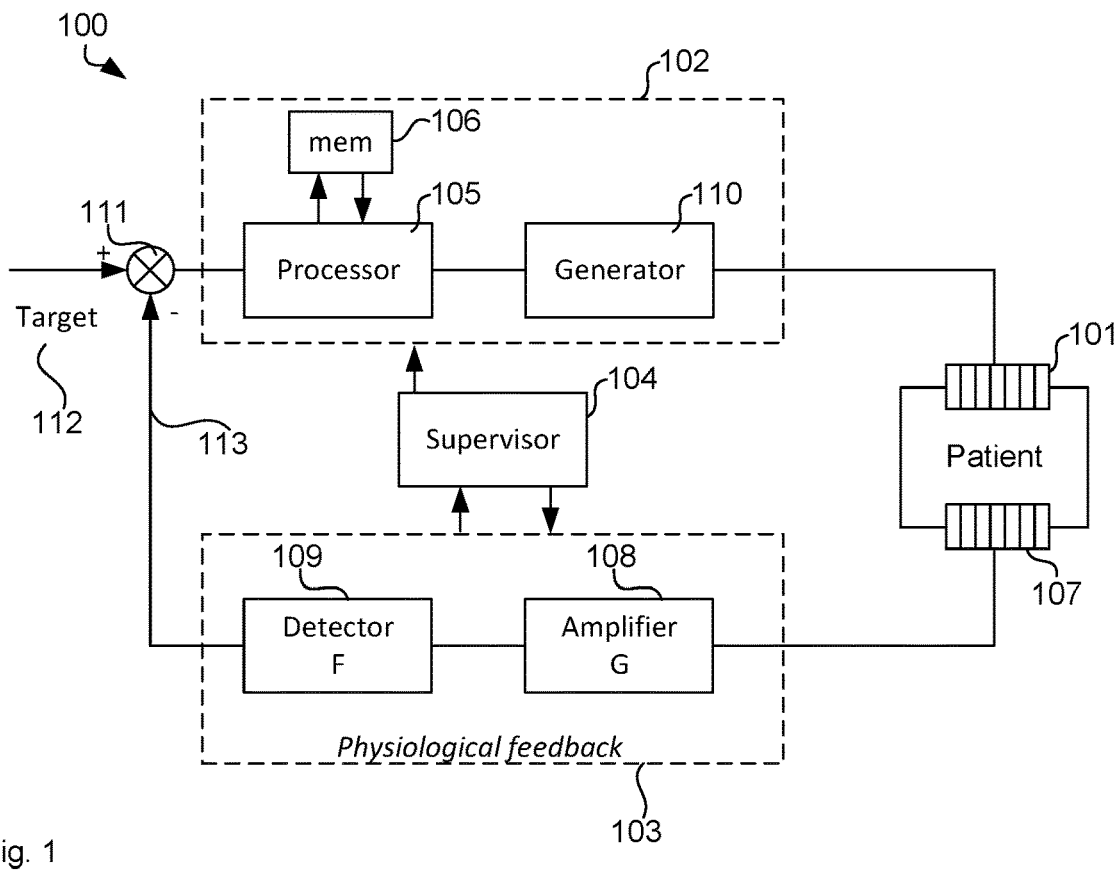
FIG. 1 illustrates an implantable neuro-stimulation device.

FIG. 1 illustrates an implantable neuro-stimulation device 100 comprising multiple stimulation electrodes 101 configured to deliver stimulation energy to neural tissue, a stimulator 102, a feedback signal 103 and a supervisor 104. Stimulator 102 comprises a microprocessor 105 and program memory 106 with program code stored thereon. The program code, when executed by the microprocessor 105, causes the microprocessor 105 to perform closed-loop control of the stimulation energy based on a feedback signal 103 that is indicative of an evoked neural response. More particularly, there is a subtracter 111 between a target stimulus 112 (set by a clinician or the patient) and the measured response 113. Processor 105 adjusts the stimulation current (i.e. the energy delivered over time) so that the output of subtracter 111 is closer to zero. It is noted that FIG. 1 depicts logical blocks, which can be combined in multiple different ways. For example, subtracter 111 and detector 109 (including an ADC fed by amplifier 108) may be implemented in software also installed on memory 106. In other examples, the modules are hardware components and/or analog implementations.

In one example, there are feedback electrodes 107 (also referred to as recording electrodes) in contact with the stimulated neural tissue, which may be the same electrodes as the stimulation electrodes or stimulation and feedback electrodes are dynamically chosen subsets from the entire number of electrodes. In the feedback signal path there is an amplifier 108 and a detector 109 of a evoked compound action potential (ECAP) signal.

Supervisor 104 detects malfunction of the stimulator based on the feedback signal. Supervisor 104 is connected to the stimulator 102 to provide a status signal indicative of the charge delivered to the stimulator. Supervisor changes the status signal to indicate malfunction upon detecting malfunction based on the feedback signal 103.

Malfunction in this context means that the feedback signal 103 has characteristics that are outside the nominal operation of the device 100. This may include clipping of amplifier 108 as described below or an ECAP signal that is outside a normal range, such as too low or too high. Other characteristics of the feedback signal may equally lead to an indication of malfunction. In this sense, malfunction means that there is inadequate stimulation due to an impaired or defective device, a deficient or flawed firmware installed on the device or due to soft errors, degradation (ageing), electrode movement, ingrowth or other effects that impact the device.

The feedback signal may be at least one of an Evoked Compound Action Potential (ECAP), a Late response (neurological response evoked between 1-10 ms after the stimulus onset), an evoked muscle response, in the absence of evoked responses it may be physiological background noise.

The measure of the late response in some embodiments comprises a record of substantially the entire duration of the late response. In the case of the subthalamic nucleus the measure of the late response in some embodiments may encompass a time period beginning 1-5 ms after the stimulus onset, more preferably beginning 1.5-4 ms after the stimulus, more preferably beginning 2-3 ms after the stimulus. In the case of the subthalamic nucleus the measure of the late response in some embodiments may encompass a time period ending 5-10 ms after the stimulus, more preferably ending 5.5-8 ms after the stimulus, more preferably ending 6.5-7.5 ms after the stimulus onset. It is to be noted that the late response as referred to herein may comprise multiple neural responses, so that the measure of the late response may comprise multiple maxima and minima as described in US 2016/0287126 A1.

Stimulator 102 is configured to adjust the control of the stimulation energy in response to the status signal from the supervisor 104 indicating malfunction. Another reason for indicating malfunction may be out of compliance of the current source, that is, the generator 110. For example, malfunction by be indicated due to excessive on insufficient stimulation current or other indicators that may be monitored by supervisor 104. In some examples, the conclusion of malfunctions depends on a combination of factors, such as the combination of the stimulation current being at a maximum value while, at the same time, the feedback signal indicating a below-target response as will be described in more detail below.

In one example, processor 105 may perform a proportional-integral-differential (PID) control process that is implemented as software on program memory. Other control methods, pure integral control or pure proportional control, may also be used.

While examples herein relate to a processor with program memory and a software implementation, the supervisor 104 disclosed herein may equally be used to monitor the feedback signal 103 by a hardware controller, such as an ASIC, or other hardware implementation of a PID or other control. For example, in some applications, a proportional control may be sufficient that can be implemented by a relatively simple comparator. However, such an control process may have the risk of developing oscillations or overshoots that may cause instability of the stimulation and/or overstimulation. In those cases, the supervisor 104 can equally disable stimulation as described herein when an ECAP value is above a set threshold.

In one example, processor 105 has integrated power electronics to drive electrodes 101 directly. In that case, the supervisor 104 may provide the status signal as an interrupt to processor 105 that has an interrupt handling routine which adjusts the stimulation energy on stops stimulation in response to the interrupt being raised. Alternatively, there may be a switch, such as a transistor in the power signal to the electrodes that is turned off by the status signal from the supervisor 104.

In another example, as shown in FIG. 1, the stimulator has a separate generator module 110 that includes the power electronics to drive electrodes 101. In particular, generator 110 may comprise current sources, such as current mirrors, to drive an adjustable stimulation current into the electrodes 101. The stimulation current is adjustable in amplitude and duration to change the amount of energy/charge that is being delivered. Generator 110 may also include a memory or shift register in cases where the number of control signals for the current sources and other elements of the generator are more than the number of bits in the output signal of the processor, such as more than 8 signals/bits or more than 16 signals/bits.

Figure 2:
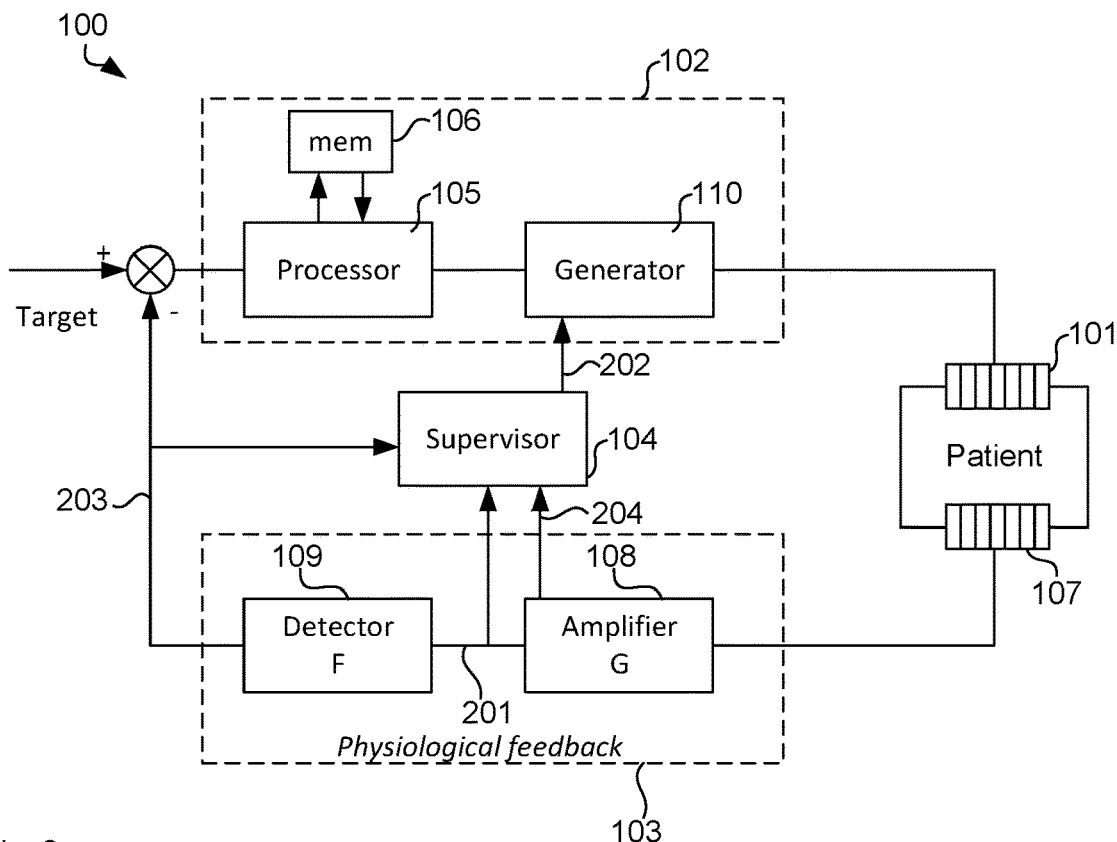
FIG. 2 illustrates another example of the device of FIG. 1.

FIG. 2 shows another example where supervisor 104 is connected to an amplifier output signal 201 between amplifier 108 and detector 109 as an input and provides a status signal 202 to generator 110. In that case, the status signal is basically an enable signal that gets deactivated upon non-compliance being detected so that stimulation is stopped regardless of the activities by processor 105. For example, supervisor 104 may read the current amplitude from amplifier 108 and when the amplitude is greater than a threshold, such as the user provided maximum sensed signal, supervisor 104 deactivates the enable signal 202 to indicate malfunction.

In other examples, supervisor 104 reads an output signal 203 from detector 109 that indicates the actual intensity of the detected ECAP signal rather than the amplitude on the amplified signal 201. Supervisor 104 can then compare the detected ECAP to a predefined maximum ECAP threshold value and raise the malfunction signal when the ECAP is above the threshold. In yet another example, amplifier 108 has a separate clipping signal 204 that indicates when the input from sense electrodes 107 is above a maximum input voltage for amplifier 108 to work optimally (i.e. linearly). A clipping signal may also be provided by an ADC when the input signal is at or above the maximum value that would encode a maximum digital signal, such as "11111111" or "00000000" for an (unsigned) 8-bit signal.

In one example, the signal is said to be clipped if at least one sample over a single stimulus's processing period is outside the clipping range specified, which may be 1.8 mV for high gain and 7.2 mV for low gain, for example. In this case, processor 105 does not update the stimulus current for the next stimulation event when in closed-loop mode but uses the present stimulus current. That is, processor 105 temporarily stops the control feedback and keeps the stimulation constant. If ADC clips for at least one sample within each of 4 consecutive stimuli, processor 105 checks the connection of the recording electrodes 107:

In closed-loop mode:
1) If any electrodes 107 are disconnected (as can be detected by the out-of-compliance signal):
   a) Stimulation is stopped. The patient is allowed to try to restart stimulation; or
   b) If disconnected, processor 105 reverts to open-loop mode until stimulation stops. If stimulation is restarted, processor 105 enters closed-loop mode.
2) If all electrodes 107 are connected (e.g. artefact is high), then:
   a) If in high-gain amplifier mode, processor 105 reverts to low-gain mode and clear ADC clipping counters. The stimulation continues in closed-loop mode.
   b) If in low-gain amplifier mode, processor 105 stops stimulation, halves the FBV target and enter Fallback mode.
   c) If in low-gain amplifier mode, processor 105 reverts to open-loop mode until stimulation stops. If stimulation is restarted, processor 105 enters closed-loop mode In open-loop mode:
1) If any electrodes 107 are disconnected, then processor 105 logs the disconnection event and continues stimulation.
2) If all electrodes 107 are connected and the ERT amplifier is in high-gain mode, processor 105 switches to low-gain mode and clear the ADC clipping counters. Processor 105 logs that the ERT amplifier gain has changed.

Figure 3:
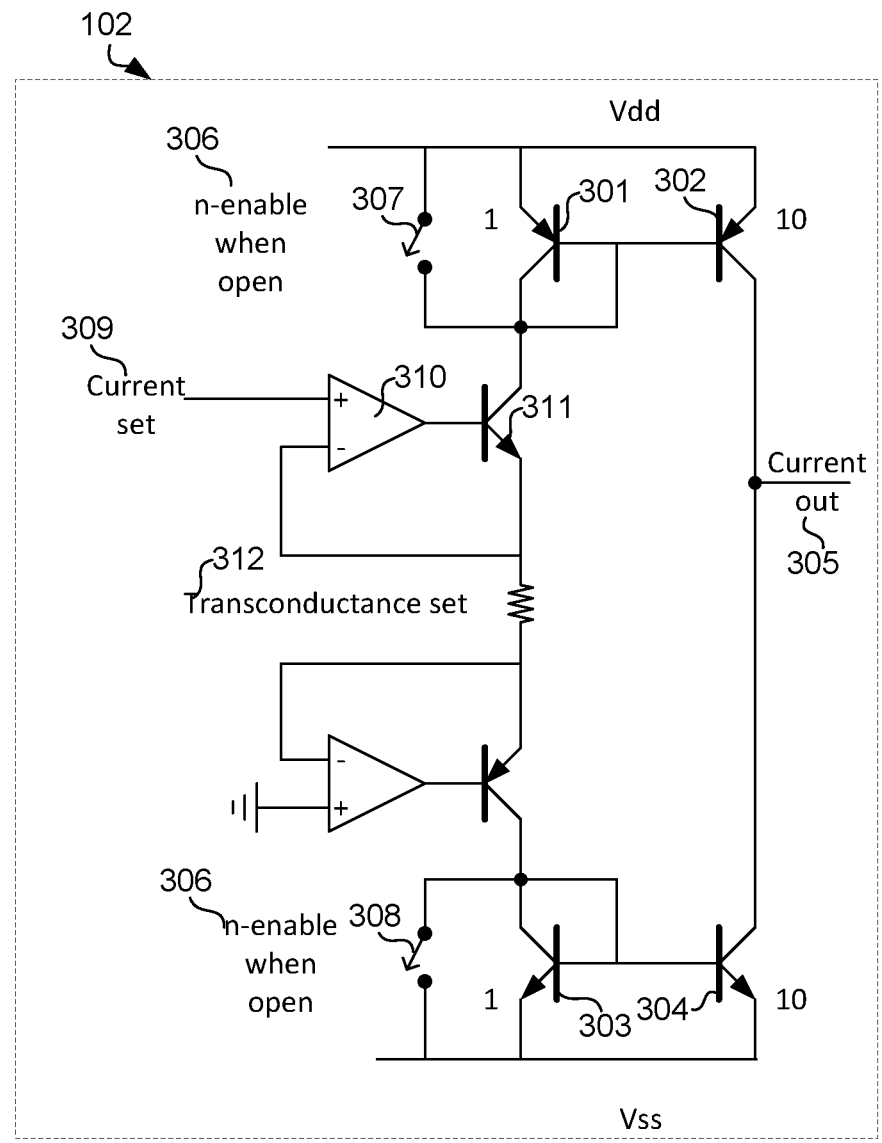
FIG. 3 illustrates the generator from FIGS. 1 and 2 in more detail.

FIG. 3 illustrates analog generator 102 in more detail. Generator 102 comprises a current source in the form of two current mirrors comprising four transistors 301, 302, 303, 304 that essentially mirror the current through transistor 301 (which is nearly the same as through 303 due to matched sizing) onto a current out signal 305. Microprocessor 105 is programmed to provide a current source activation signal 306 to the current source to activate (open switches 307, 308) and de-activate (close switches 307, 308) the current source. These switches control the time current is enabled to the output which controls the amount of charge delivered by the stimulation electrodes 101. The amount of charge may further be controlled by setting the current through an analog current set signal that is decoupled by an amplifier 310 and controls a control transistor 311 which, in turn, controls the reference current through transistor 301 and therefore the amplitude of the current out signal 305.

The control of the stimulation energy can be adjusted by way of a hardware circuit that disables stimulation. For example, supervisor 104 (not shown in FIG. 3) provides a status signal which may be the input to an NAND gate that switches to 'HIGH' if the status signal switches to 'LOW' and the output of the NAND gate can form the activation signal 306. As a result, in response to the status signal from supervisor 104 indicating malfunction, stimulation is stopped by closing switches 307 and 308. This occurs regardless of the activation signal provided from processor 105, which would be the second input to the NAND gate but effectively masked by a 'LOW' on the first input from the status signal. In other examples below, the status signal gates a clock signal provided to the generator.

In other examples, the microprocessor is programmed by way of an interrupt routine, to adjust the control of the stimulation energy by stopping stimulation, adjusting an amplifier gain of amplifier 108 in feed-back loop 103 (see FIG. 1), adjust a stimulation level and enable/disable closed-loop therapy.

It is noted that the circuit implementations provided herein are merely an example and a wide range of implementations may be used to achieve the desired outcome of charge monitoring, such as analog circuits, ASICs, FGPAs, further microcontrollers, custom transistor circuits etc. In particular, the analog circuit of FIG. 3. may be implemented in digital form.

In addition or as an alternative to the clipping signal, supervisor 104 may also monitor the ECAP value 203 from detector 109 as mentioned above. ECAP value 203 may also be referred to as feedback value (FBV) since it is subtracted from a target value and the result used as the error signal in a PID control (or P or I only). In one example, stimulation is stopped when the stimulation current is at its limit for a predefined period of time, such as 100 ms, and the measured ECAP is less than a predefined fallback target, such as ½ of the target FBV. Supervisor 104 may be connected to current set signal 309 to read the stimulation current or may be connected to a digital control signal that encodes the stimulation current as a bit vector. In one example, supervisor 104 detects maximum stimulation current if the bit vector comprises all 1s (such as 11111111 for 8-bit). When stimulation is restarted by the Patient, closed loop therapy may resume when the FBV exceeds the new target for two consecutive stimuli.

Figure 4:
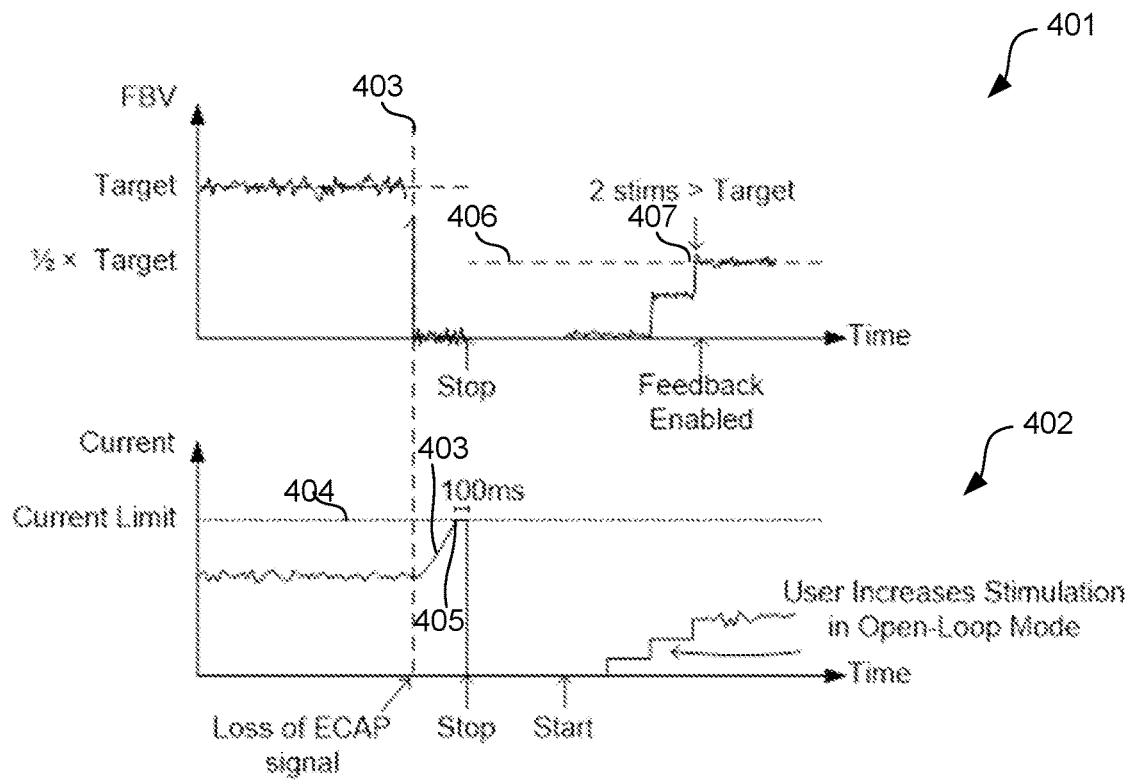
FIG. 4 illustrates an feedback value and stimulation current over time.

FIG. 4 illustrates an example FBV 401 and stimulation current 402 over time. At point 403 an unidentified problem occurred where the FBV dropped. This may have happened as a result of the sensing electrodes 107 (see FIG. 1) losing connection to the tissue. In this case, the stimulation still occurs but it is not measured anymore. As a result of integral control, for example, processor 105 increases the stimulation current as shown at 404 until the stimulation current reaches a maximum 404 at time 405. This is undesirable because the patient may perceive significant pain due to excessive stimulation. Therefore, supervisor 104 monitors the FBV and in this example also the stimulation current. In this example, after detecting FBV below ½ the target for more than 100 ms, the supervisor 104 indicates malfunction and processor 105 or transistor 307 stops stimulation. The user may then re-start stimulation in open-loop mode (no control feedback/fixed stimulation current) and gradually increase the stimulation current. When the FBV reaches ½ target as shown at 407, feedback/closed-loop control resumes.

Figure 5:
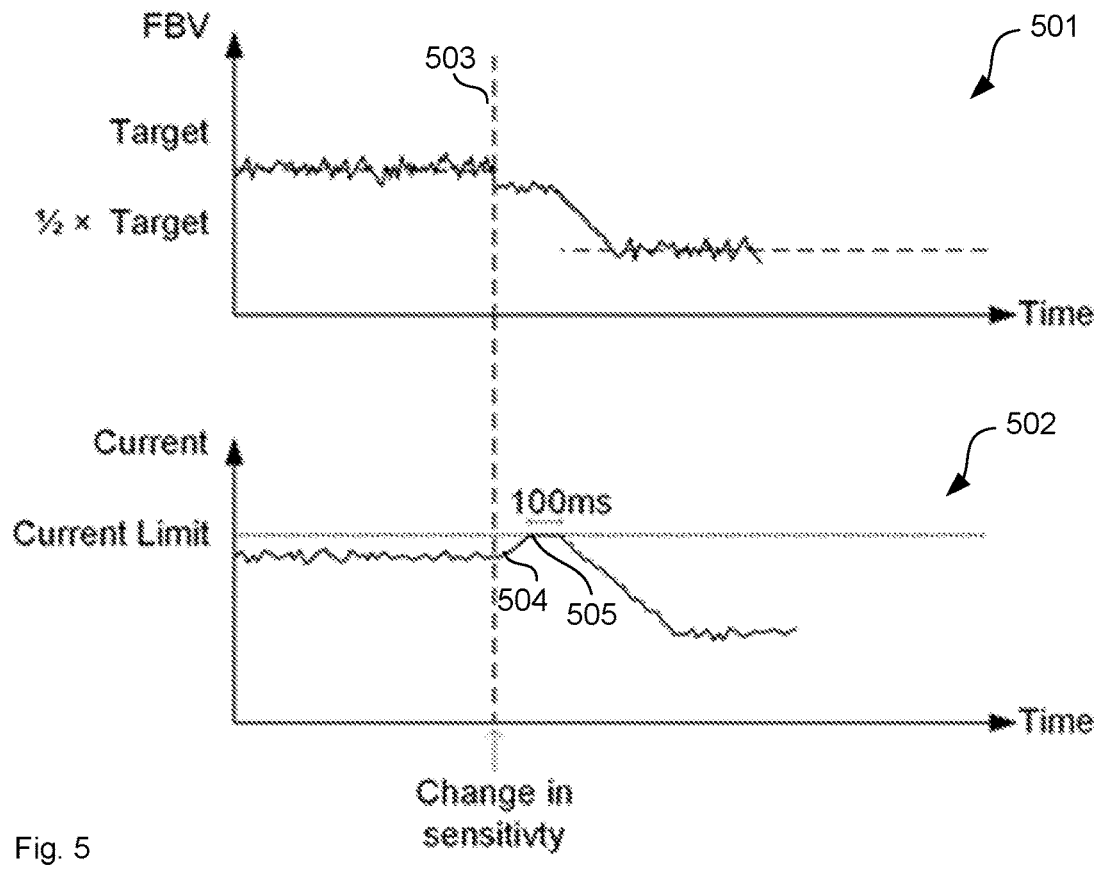
FIG. 5 shows another example of the feedback value and the stimulation current where the stimulation current increases as a change in sensitivity results in a smaller feedback value.

FIG. 5 shows another example where current increases as a change in sensitivity results in a smaller FBV. In particular, FIG. 5 shows again FBV 501 and stimulation current 502 over time. At a first point in time 503, the sensitivity reduces suddenly, which leads to a decreased FBV, which is now well below the target but still above ½ FBV target. Again, processor 105 performs pure integral (I) control, which leads to a gradual rise in the stimulation current 504 until, at point 505, the stimulation current reaches the maximum stimulation current. After the stimulation current remains at the limit for a predefined period of time, such as 100 ms, processor 105 halves the feedback target (if ECAP is greater than the fallback target (½ Target)). After that, stimulation continues in closed loop mode in the sense that the closed loop control process aims to maintain the FBV at the reduced target. It is noted that the above examples in FIGS. 4 and 5 use ½ target FBV as a fall-back target but other values may equally be used, such as ¾ or ¼ target FBV. The overarching mechanism is that when the stimulation current reaches its maximum, stimulation is stopped if the FBV has changed by a relatively large amount. Alternatively, the stimulation target is reduced if the FBV has changed by a relatively small amount. In the examples of FIGS. 4 and 5, relatively large is below ½ target FBV and relatively small is above ½ target FBV.

The rationale for such a fall-back mode may be as follows: If the stimulation current reaches its limit and the recording electrodes are still connected, it suggests that either: the feedback target is too high (which can be ignored as the clinician will set the value to a reasonable one); or because patient sensitivity has decreased (so a given stimulation current suddenly results in a smaller FBV). This means the original target cannot be reached and so, lost control of the loop. This situation may arise if a lead migrates in the epidural space, for example. By setting the target to half its present value, the change in sensitivity is accounted for by setting the target to a value that can be achieved by a stimulation current within its limit and is therefore able to be controlled.

Supervisor 104 may provide an error signal to processor 105 to indicate different type of errors that can be logged on memory 106 for later readout by a clinician or technical specialist. Further, processor 105, generator 110 and supervisor 104 (and potentially memory 106) may be integrated into a single chip where the boundaries between the modules are practically invisible.

In other examples, supervisor 104 may supervise further parameters of the implantable device 100, including stimulation pulse validity, out-of-compliance of the current source, clock error, disconnection of stimulation electrodes or the recording electrodes, and/or possible noise due to charging.

Not a Valid Stimulation Pulse

There are circumstances in which the delivered stimulation pulse is invalid. For example, the stimulation amplitude can be affected, while reference clock error is an indication that stimulation pulse width has been affected.

Out-of-Compliance

Figure 7:
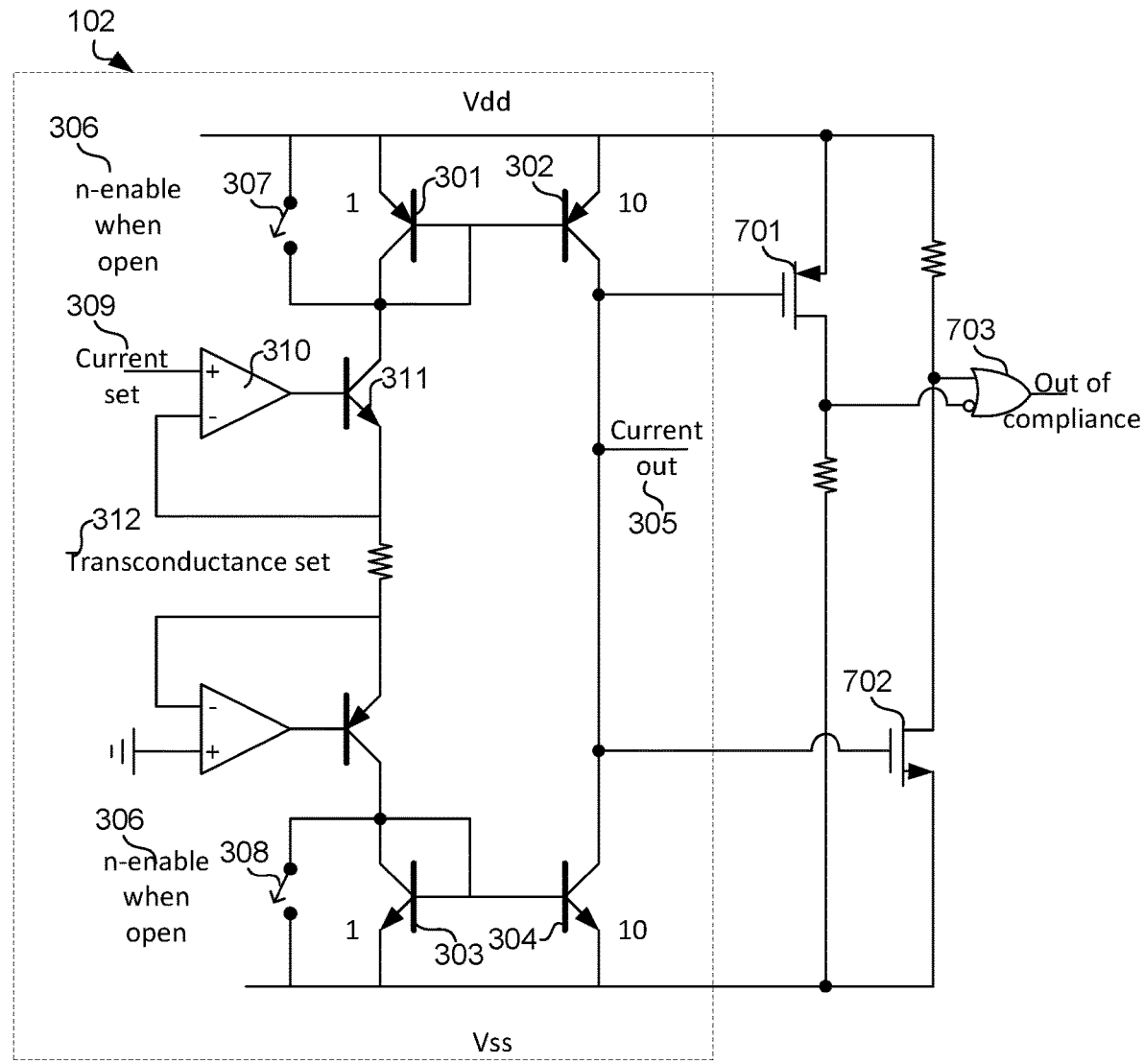
FIG. 7 illustrates the generator from FIG. 3 with an additional circuit to generate an out of compliance signal.

Supervisor 104 checks that the system is in compliance and if not, attempts to restore compliance by reducing the current in closed-loop mode and may not allow the patient to increase the stimulus current in open loop mode. FIG. 7 illustrates an example circuit where the current source described with reference to FIG. 3 generates the out of compliance signal. In particular, there are two transistors 701 and 702 and an AND gate 703 with one inverted input. If one of the transistors is on, the output of the logic gate is '0' indicating no out of compliance. However, if both transistors are off, out of compliance is indicated by a '1' output signal. In one example, the transistors 701, 702 are FETs and their threshold value is about 0.6 V. The out of compliance signal is connected to the supervisor 104 in FIGS. 1 and 2. This connection is not shown in those figures for clarity.

When malfunction, such as out of compliance, is indicated, the system may check the connection of each stimulation electrode:

1) If any of the stimulation electrodes 101 are disconnected, then stimulation is stopped.
2) Otherwise:
   a) For the closed-loop case: Processor 105 halves the FBV target:

i) if the measured ECAP is less than or equal to the new FBV target, processor 105 stops stimulation and enters Fallback mode be entered.

ii) If the measured ECAP is greater than the new FBV target, processor 105 continues stimulation in closed-loop mode.

b) For the open-loop case: processor 105 continues stimulation, then if:

i) the Patient is not able to increase the current level (from the remote control).

ii) the CPA Operator can increase the current level, even though the current output will be limited by the voltage.

Reference Clock Error

The supervisor 104 checks the integrity of the stimulation pulse width and if invalid, revert to open-loop for that period. During stimulation, processor 105 monitors for reference clock errors and reverts to open-loop mode for that period if it is active. If the error occurs two or more times within number of consecutive stimuli, processor 105 stops stimulation. The number of consecutive stimuli may have a default value of 7 on reset, and may be configurable in a range of 1 . . . 100.

It is noted that a reference clock error may be generated by the generator 110 and is an indication that the reference clock is out of specification. The implication of this is that the timing used to generate the stimulation pulse is incorrect and therefore the stimulation pulse width is not trusted.

Recording Electrode Disconnected

The supervisor 104 checks the connection of the recording electrodes 107, and if they are disconnected, then the stimulator 100 reverts to open-loop therapy or stop stimulation. When the clinician or patient instructs the system 100 to start stimulation the system checks the connection of each of the multiple electrodes 101/107:

1) If one or more stimulation electrodes 101 are disconnected, then processor 105 does not start stimulation.

2) If one or more recording electrodes 107 are disconnected:

a) For open-loop only firmware or when starting in open-loop mode: stimulation starts.

b) When starting in open-loop mode: stimulation may not start.

c) For closed-loop enabled firmware when starting in closed-loop mode:

i) Processor 105 may revert to open-loop mode until stimulation stops.

ii) The stimulation may not start.

In closed-loop mode, if the stimulation current is at its maximum setting for 100 ms, supervisor 104 checks the connection of the recording electrodes 107.

1) If one or more recording electrodes 107 are disconnected—processor 105 stops the stimulation and the patient is allowed to try and restart.

2) Else:—processor 105 continues stimulation and halves the FBV target. Then:

a) If the measured ECAP is greater than the new target, then processor 105 continues in closed-loop mode b) If the measured ECAP is less than the new target, processor 105 stops stimulation and enters Fallback mode; then:

i) If the Patient starts stimulation, then processor 105 starts in open-loop mode, then closed-loop mode is re-enabled if at least 2 consecutive FBVs are above the FBV target ii) If the operator starts stimulation, then processor 105 starts in the mode configured from the operator. The Fallback mode condition is cleared.

iii) If the program is changed by the Patient, the Fallback mode condition is cleared, then when the patient starts stimulation, processor 105 start as no Fallback mode condition had occurred.

Possible Noise

Supervisor 104 may further generate a possible noise indicator, or processor 105 may receive the possible noise indicator signal from a telemetry microcontroller. This signal indicates the existence of noise in the system that may affect the neural response measurement performance. In one example, this signal is indicative of battery charging or RF communications, such that the possible noise input is enabled whenever the stimulator's battery is being charged.

Figure 6A:
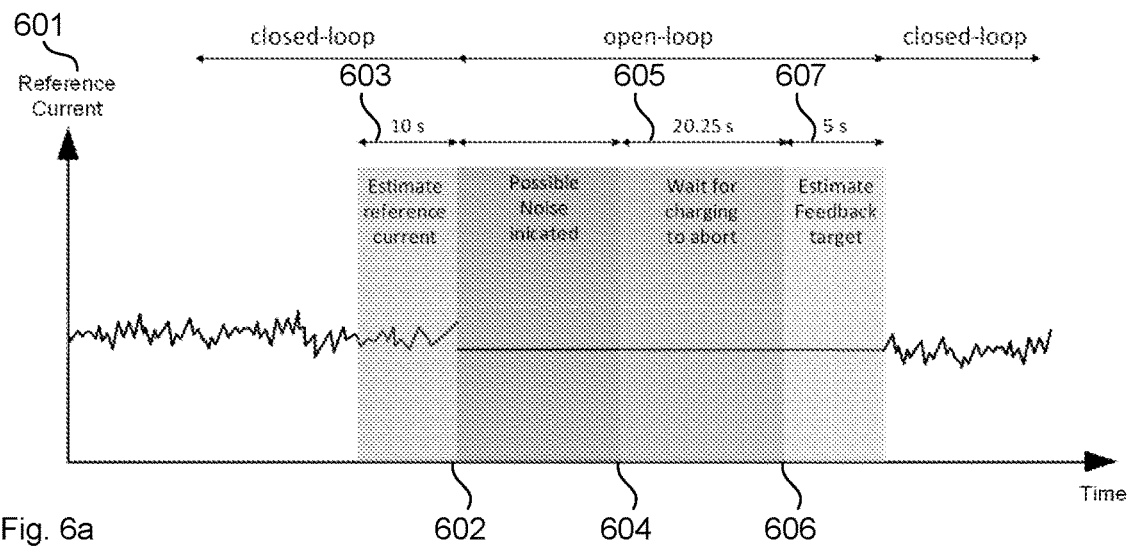
FIG. 6a illustrates an example of switching between closed-loop and open-loop control.

During stimulation, the processor 105 monitors the Possible Noise input, and reverts to open-loop mode if it is active. FIG. 6a illustrates an example of switching between closed-loop and open-loop control. In particular, FIG. 6a shows the reference current 601, which is the current through transistors 301 and 311 in FIG. 3 as set by the current set signal 309. Reference current is synonymous with stimulation current above. In this example, charging starts at a first point in time 602. Processor 105 sets the reference current in open-loop mode to the minimum reference current in the previous 10 seconds 603.

When the Possible Noise input clears at a second point in time 604, processor 105 retains stimulation in open-loop mode for the time 605 taken for charging to be aborted due to a loss of communication, which may be 20.25 seconds, for example. If the Possible Noise input remains inactive after third point in time 606, processor 105 estimates the feedback target over a estimation period 607, which may be 5 seconds, for example. Processor 105 then returns stimulation to closed-loop mode and sets the feedback target to the minimum of the current feedback target and the average feedback variable magnitude measured over the 5 second estimation period.

The rationale for averaging reference current when reverting to open-loop mode may be described as follows: Applying an energised charger coil introduces noise which interferes with measuring ECAPs. In some cases, the ECAP magnitude is reduced. In closed-loop mode, this results in the reference current (and therefore the delivered stimulation) suddenly increasing, which can be discomforting for the patient. Setting the reference current to the minimum value over the previous ten seconds is performed with the aim of minimising discomfort. The ten second window 603 is considered long enough to mitigate sudden jumps in stimulation current, even if coupling the charger is difficult.

The rational for estimating feedback target when returning to closed-loop mode may be described as follows: During charging, communication (coupling) may be lost between the charger and implant resulting in the Possible Noise input being cleared. However, the charger will remain energised for a charger wait time 605 (e.g., 20.25 seconds) attempting to re-establish communication. If communication cannot be re-established, charging is aborted. Estimating the feedback target when the charger is energised may result in the feedback target being set incorrectly. By waiting for the charger to timeout (20.25 seconds) the feedback target can be estimated more reliably. Estimating over a 5 second window is considered long enough to account for the impact of heart rate on the ECAP, as well as, any postural change associated with removing the charger.

Figure 6B:
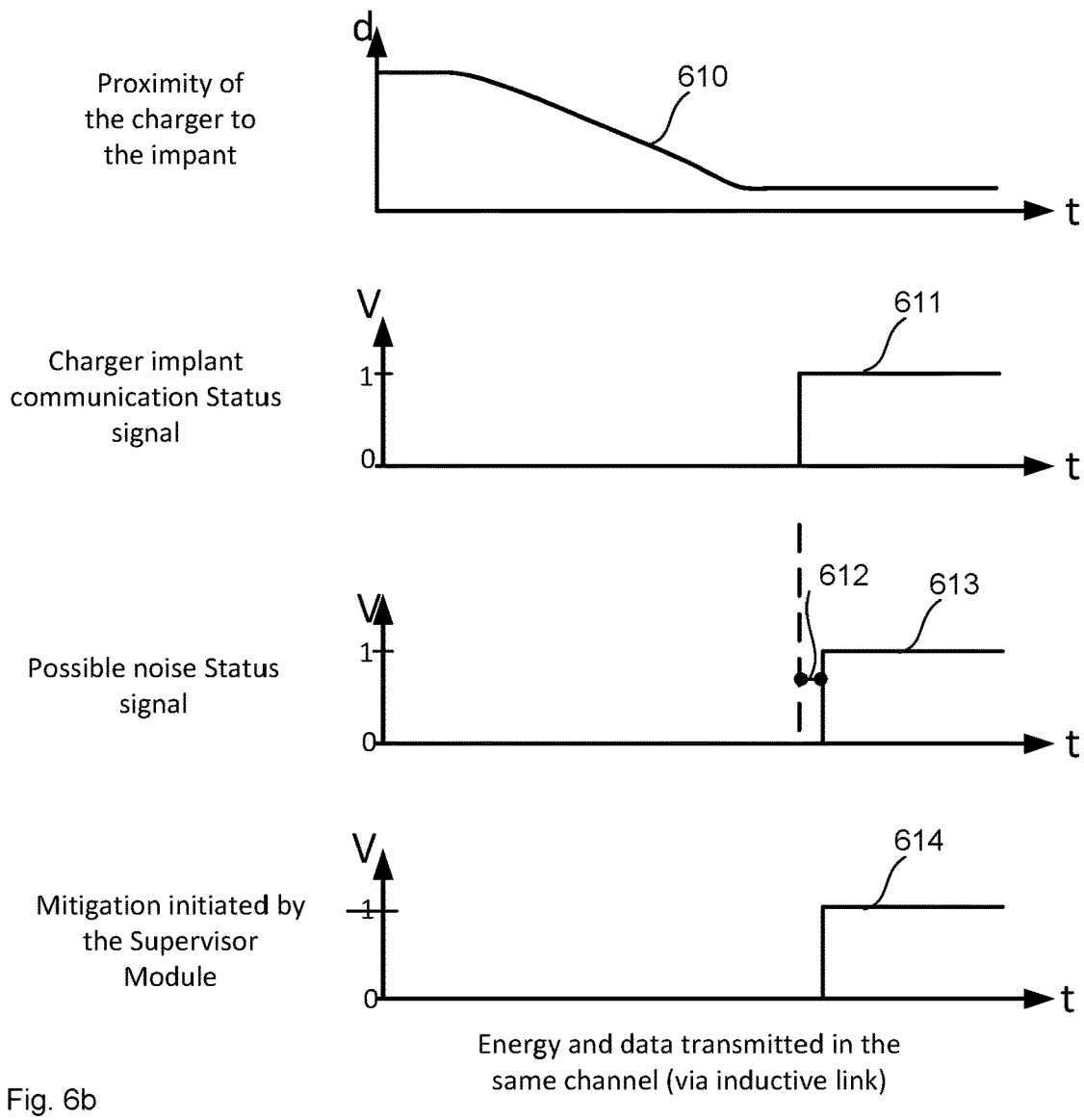
FIG. 6b illustrates signal waveforms related to a charging event.

FIG. 6b illustrates signal waveforms related to a charging event. As the external charging devices is brought into position, the distance 610 between the charging device and the implant falls. A charger implant communication status signal 611 is then activated and after a delay 612, the possible noise status signal 613 is activated, which in turn activates the mitigation 614 initiated by the supervisor.

Digital Core Integration

In one example, the supervisor 104 is instanced in the controller 105 (digital_core module) together with the stimulator 102 and feedback 103 in a single chip. This allows it to get in between the detector 109 and the analog interface so it can disable stimulus when it detects an error and allows its status to be easily read using the control interface along with the other status bits.

Supervisor 104 can provide an error type signal to processor 105. In turn, processor 105 creates a record on memory 106 of the error type signal. This way, a user, such as a service personnel or a clinician can read-out the error type and discern any problems with the stimulator device 100. In response, the stimulator 100 may be configured differently, such as by changing the desired evoked response, disabling feedback control to switch to open loop control.

In one example, the clk_error signal is a top-level input. This is because it comes from the clk_check module that is now part of the sys_ctrl module. The reason for this is that clk_check now works on the clkref2m clock instead of qclk. This makes the frequency check more accurate (1.6% error instead of 5%) and faster (30.5 us instead of 244 us).

Figure 8:
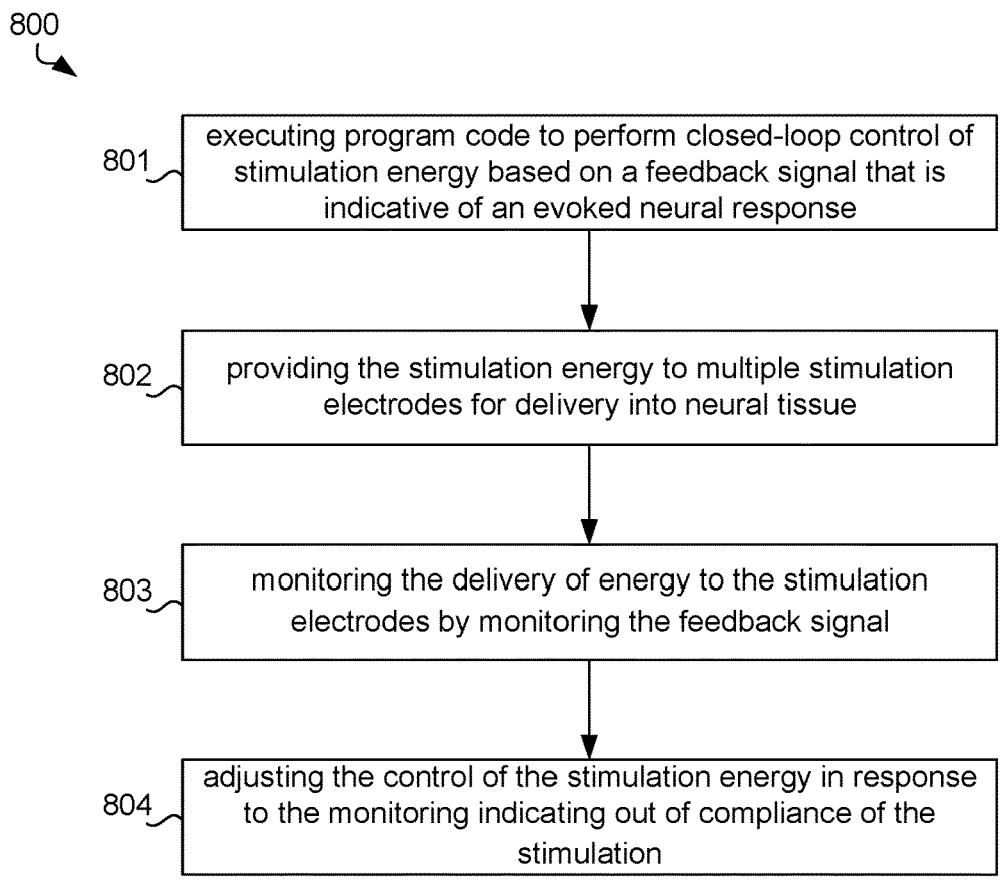
FIG. 8 illustrates a method for neural stimulation.

FIG. 8 illustrates a method 800 for neural stimulation. The method comprises the steps of executing 801 program code to perform closed-loop control of stimulation energy based on a feedback signal that is indicative of an evoked neural response as described above. Then, the stimulation energy is provided 802 to multiple stimulation electrodes for delivery into neural tissue A supervisor monitors 803 the delivery of energy to the stimulation electrodes by monitoring feedback signal 103. Finally, the control of the stimulation energy is adjusted 804 in response to the monitoring indicating malfunction of the stimulation as also described herein.

In summary, the supervisor monitors the out-of-compliance indicators in the current sources in the stimulator, the loop controller, possible noise, reference clock error, and the ADC in the detector to detect conditions that:
stop stimulation;
adjust ERT amplifier gain;
adjust the stimulation level;
enable/disable closed-loop therapy (applies to both commercial and study versions of closed-loop firmware, refer to Section 6), Further, the supervisor monitors the feedback loop and is separate from the other mechanisms that limit stimulus during fault conditions within in the system.

While in some of the examples above, the supervisor 104 is connected to the feedback signal, it is noted that in addition or as an alternative, supervisor 104 may be connected to the stimulation circuitry comprising processor 105 or generator 110 or both. Supervisor 104 mal also read data from memory 106. Accordingly, supervisor 104 may be configured to detect at least one error condition of the stimulator 100 based on the reading from processor 105, generator 110 or memory 106. As a result, supervisor may indicate the at least one error condition to the processor 105. The error condition may be indicative of at least one inconsistency, which includes the conditions described throughout this disclosure. For example, supervisor 104 may monitor the FBV 113 and determine whether the FBV rises or falls with a rise or fall in stimulation current, respectively. That is, if the FBV remains unchanged with a change in stimulation current, supervisor 104 flags this as a problem.

Figure 9:
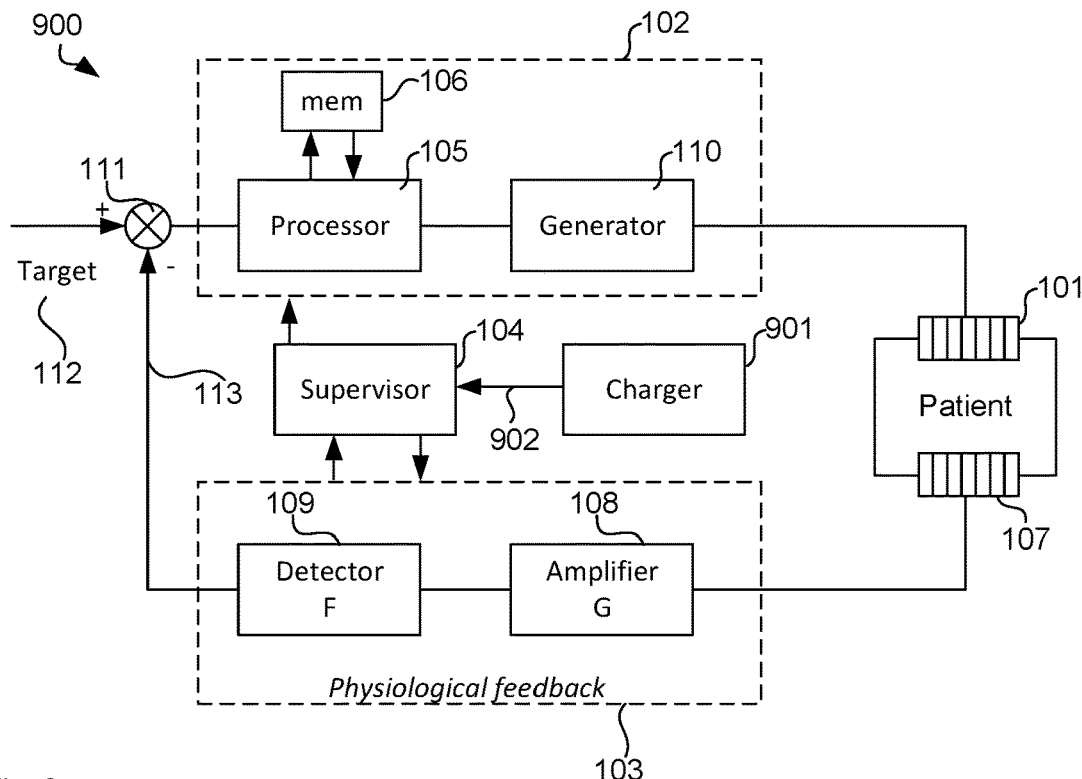
FIG. 9 illustrates the stimulation device from FIG. 1 with an additional charger.

FIG. 9 illustrates another example of device 900, which has the same components as device 100 in FIG. 1 with the addition of a charger 901. The charger 901 provides a charging signal 902 to supervisor 104. The charging signal 902 may indicate current charging as described above with reference to FIG. 6a. In another example, charging signal 903 indicates an anticipated charging event. For example, the user may have an external charging device with an additional button to prepare stimulation device 900 for charging. When the user presses that button, the external charging device initiates communication over an RF link to send a message to stimulation device 900 indicating and anticipated charging event. In particular, charger 901 receives this message (such as forwarded by processor 105) and raises the charging signal 902. This way, uncomfortable stimulation levels can be avoided during the time between charging (i.e. noise) commences and the charging signal being raised.

Figure 10:
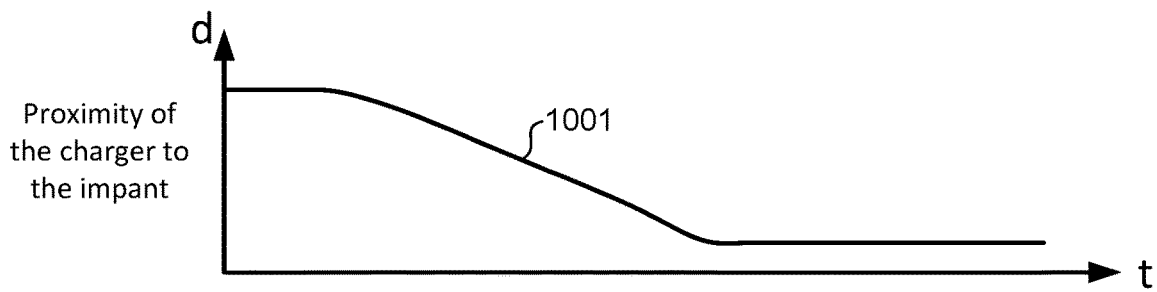
FIG. 10 illustrates example waveforms that may be generated in connection with the stimulation device and charger of FIG. 9.
Figure 10:
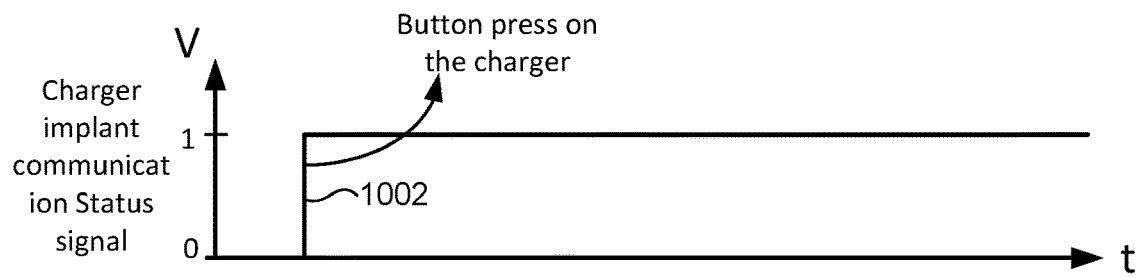
Figure 10:
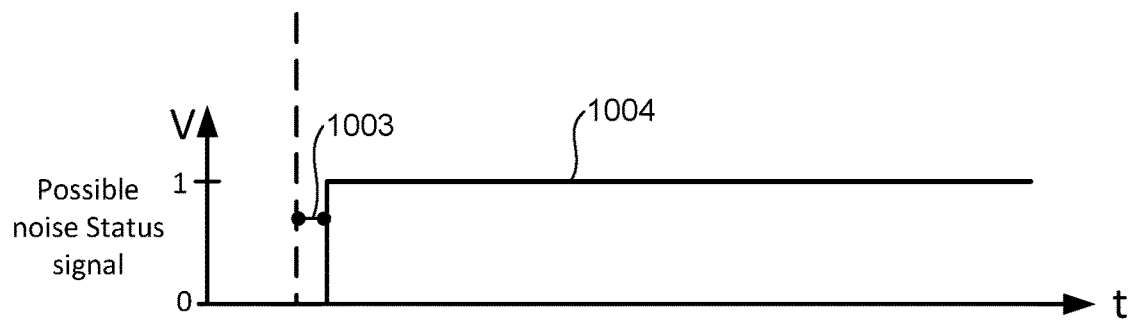
Figure 10:
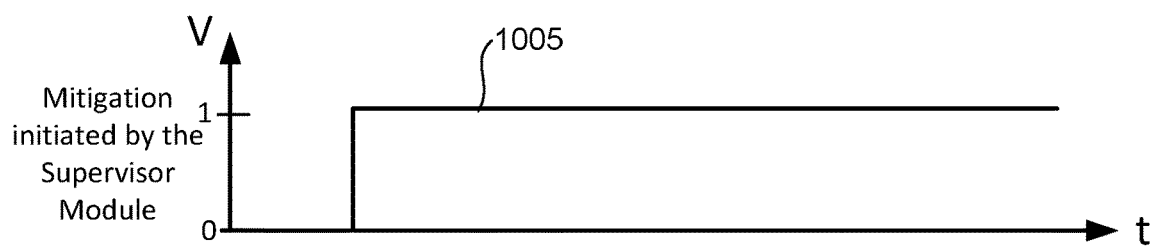

FIG. 10 illustrates example waveforms that show how the external charging device is brought into proximity 1001 to the implant. In contrast to FIG. 6b, however, the user now presses the charging button as described above, which causes the charger implant communication signal 1002 to rise before the external charging device is close enough for charging. After a short delay 1003, this results in an activation of the possible noise status signal 1004 and commencement of the mitigation 1005 initiated by the supervisor module well before the charging starts and the noise could cause uncomfortable stimulation levels.

It will be appreciated by persons skilled in the art that numerous variations and/or modifications may be made to the above-described embodiments, without departing from the broad general scope of the present disclosure. The present embodiments are, therefore, to be considered in all respects as illustrative and not restrictive.

The invention claimed is:

1. An implantable neuro-stimulation device comprising:
   a stimulator configured to control delivery of stimulation energy to neural tissue, the stimulator further configured to perform closed-loop control of the stimulation energy based on a feedback signal that is indicative of an evoked neural response;
   a supervisor
      connected to the feedback signal,
      configured to detect malfunction of the stimulator based on the feedback signal;
      connected to the stimulator to provide a status signal to the stimulator; and
      configured to compare the feedback signal to a desired feedback value and to change the status signal based on the comparison to indicate malfunction upon detecting malfunction based on the feedback signal;
   wherein the stimulator is configured to adjust the control of the stimulation energy by reducing the desired feedback value in response to the status signal from the supervisor indicating malfunction.

2. The device of claim 1, wherein
   the feedback signal is indicative of a feedback value representing one or more of:
      measured evoked response,
      late response, and
      evoked muscle response.

3. The device of claim 1, wherein the stimulator is configured to halve the desired feedback value upon the status signal indicating malfunction.

4. The device of claim 1, wherein the stimulator is configured to perform mitigation upon the status signal indicating malfunction after reducing the desired feedback value.

5. The device of claim 1, wherein the supervisor is connected to the feedback signal through an amplifier that amplifies the feedback signal to detect clipping of the amplifier and the supervisor is configured to change the status signal to indicate malfunction based on the clipping of the amplifier.

6. The device of claim 1, wherein the supervisor is connected to a stimulation intensity signal that is indicative of a stimulation intensity and the supervisor is configured to compare the instant stimulation intensity signal to a maximum value and change the status signal to indicate malfunction upon determining that the stimulation intensity was at the maximum value for a predetermined period of time.

7. The device of claim 6, wherein the supervisor is configured to change the status signal to indicate malfunction upon determining that the stimulation intensity is at a maximum value and a feedback value as indicated by the feedback signal is less than a desired feedback value.

8. The device of claim 7, wherein the supervisor is configured to reduce the desired feedback value upon detecting malfunction based on the status signal and to perform mitigation upon determining that the malfunction is present after reducing the desired feedback value.

9. The device of claim 1, wherein the supervisor is further connected to one or more clock signals and configured to detect a clock error based on the one or more clock signals and change the status signal to malfunction upon determining a clock error.

10. The device of claim 1, wherein the stimulator is further configured to adjust the control of the stimulation energy in response to an out of compliance signal indicating malfunction.

11. The device of claim 1, wherein the status signal is provided to the stimulator as an interrupt signal.

12. The device of claim 1, wherein the stimulator is configured to adjust the control of the stimulation energy by one or more of:
  stopping stimulation;
  adjusting an amplifier gain of a feed-back loop;
  adjusting a stimulation level; or
  enabling/disabling closed-loop therapy.

13. The device of claim 1, wherein the stimulator or the supervisor is configured to detect the possible noise condition in the feedback signal and, upon detecting a possible noise condition in the feedback signal, to change the control of the stimulation energy.

14. The device of claim 13, wherein detecting the possible noise condition comprises detecting a charging event.

15. The device of claim 13, wherein detecting the possible noise condition is based on a signal indicating that a charging event is anticipated.

16. The device of claim 13, wherein changing the control of the stimulation energy comprises switching the control to open-loop control during the possible noise condition and switching back to closed-loop control upon determining absence of the possible noise condition.

17. A method for neuro-stimulation, the method comprising:
  performing closed-loop control of stimulation energy based on a feedback signal that is indicative of an evoked neural response;
  providing the stimulation energy into neural tissue;
  monitoring the delivery of energy by monitoring the feedback signal;
  comparing the feedback signal to a desired feedback value and to change a status signal based on the comparison to indicate malfunction upon detecting malfunction based on the feedback signal; and
  adjusting the control of the stimulation energy by reducing the desired feedback value in response to the monitoring indicating malfunction of the stimulation.

18. An implantable neuro-stimulation device comprising:
  a stimulator configured to control delivery of stimulation energy to neural tissue, the stimulator further configured to perform closed-loop control of the stimulation energy based on a feedback signal that is indicative of an evoked neural response;
  a supervisor
    connected to the feedback signal,
    configured to detect malfunction of the stimulator based on the feedback signal; and
    connected to the stimulator to provide a status signal to the stimulator;
  connected to a stimulation intensity signal that is indicative of a stimulation intensity;
  wherein the supervisor is configured to compare the stimulation intensity signal to a maximum value and change the status signal to indicate malfunction upon determining that the stimulation intensity was at the maximum value for a predetermined period of time; and
  wherein the stimulator is configured to reduce a desired feedback value for the feedback signal upon detecting malfunction based on the status signal.

19. The device of claim 18, wherein
the feedback signal is indicative of a feedback value representing one or more of:
  measured evoked response,
  late response, and
  evoked muscle response.

20. The device of claim 18, wherein the stimulator is configured to halve the desired feedback value upon the status signal indicating malfunction.

21. The device of claim 18, wherein the stimulator is configured to perform mitigation upon determining that the malfunction is present after reducing the desired feedback value.

22. The device of claim 18, wherein the stimulator is configured to adjust the control of the stimulation energy by one or more of:
  stopping stimulation;
  adjusting an amplifier gain of a feed-back loop;
  adjusting a stimulation level; or
  enabling/disabling closed-loop therapy.

23. The device of claim 18, wherein the stimulator is configured to detect a possible noise condition in the feedback signal and, upon detecting a possible noise condition in the feedback signal, to change the control of the stimulation energy.

24. The device of claim 18, wherein changing the control of the stimulation energy comprises switching the control to open-loop control during the possible noise condition and switching back to closed-loop control upon determining absence of the possible noise condition.

25. A method for neuro-stimulation, the method comprising:
- performing closed-loop control of stimulation energy based on a feedback signal that is indicative of an evoked neural response;
- providing the stimulation energy to one or more stimulation electrodes for delivery into neural tissue;
- monitoring the delivery of energy to the stimulation electrodes by monitoring the feedback signal;
- comparing a stimulation intensity signal that is indicative of a stimulation intensity to a maximum value and changing a status signal to indicate malfunction upon determining that the stimulation intensity was at the maximum value for a predetermined period of time; and
- reducing a desired feedback value for the feedback signal upon detecting malfunction based on the status signal.

26. An implantable neuro-stimulation device comprising:
- a stimulator configured to deliver stimulation energy to neural tissue, the stimulator further configured to perform closed-loop control of the stimulation energy based on a feedback signal that is indicative of an evoked neural response;
- a supervisor
  - connected to the feedback signal,
  - configured to detect malfunction of the stimulator based on the feedback signal;
  - connected to the stimulator to provide a status signal to the stimulator;
  - connected to a stimulation intensity signal that is indicative of a stimulation intensity;
- wherein the supervisor is configured to change the status signal to indicate malfunction upon determining that the stimulation intensity is at a maximum value and a feedback value as indicated by the feedback signal is less than a desired feedback value; and
- wherein the stimulator is configured to reduce the desired feedback value upon detecting malfunction based on the status signal.

27. The device of claim 26, wherein
the feedback signal is indicative of a feedback value representing one or more of:
measured evoked response,
late response, and
evoked muscle response.

28. The device of claim 26, wherein the stimulator is configured to halve the desired feedback value upon the status signal indicating malfunction.

29. The device of claim 26, wherein the stimulator is configured to perform mitigation upon determining that the malfunction is present after reducing the desired feedback value.

30. The device of claim 26, wherein the stimulator is configured to adjust the control of the stimulation energy by one or more of:
stopping stimulation;
adjusting an amplifier gain of a feed-back loop;
adjusting a stimulation level; or
enabling/disabling closed-loop therapy.

31. The device of claim 26, wherein the stimulator is configured to detect a possible noise condition in the feedback signal and, upon detecting a possible noise condition in the feedback signal, to change the control of the stimulation energy.

32. The device of claim 26, wherein changing the control of the stimulation energy comprises switching the control to open-loop control during the possible noise condition and switching back to closed-loop control upon determining absence of the possible noise condition.

33. A method for neuro-stimulation, the method comprising:
- performing closed-loop control of stimulation energy based on a feedback signal that is indicative of an evoked neural response;
- providing the stimulation energy to one or more stimulation electrodes for delivery into neural tissue;
- monitoring the delivery of energy to the stimulation electrodes by monitoring the feedback signal;
- upon determining that the stimulation intensity is at a maximum value and a feedback value as indicated by the feedback signal is less than a desired feedback value, changing a status signal to indicate malfunction;
- reducing a desired feedback value for the feedback signal upon detecting malfunction based on the status signal.

* * * * *